United States Patent [19]
Landsberger

[11] Patent Number: 6,113,599
[45] Date of Patent: Sep. 5, 2000

[54] APPARATUS FOR INTERNAL MANDIBULAR DISTRACTION

[75] Inventor: Samuel E. Landsberger, Redondo Beach, Calif.

[73] Assignee: Kalpa Engineering, Inc., Redondo Beach, Calif.

[21] Appl. No.: 09/090,454

[22] Filed: Jun. 4, 1998

Related U.S. Application Data

[60] Provisional application No. 60/048,557, Jun. 4, 1997.

[51] Int. Cl.[7] .................................................. A61B 17/56
[52] U.S. Cl. ................................ 606/60; 606/57; 606/58
[58] Field of Search ................................. 606/60, 57, 58, 606/61, 62, 63, 53, 69–77, 105; 623/16, 14; 433/7, 174

[56] References Cited

U.S. PATENT DOCUMENTS

| | | |
|---|---|---|
| 5,540,687 | 7/1996 | Fairley et al. . |
| 5,569,250 | 10/1996 | Sarver et al. ............................. 606/69 |
| 5,704,939 | 1/1998 | Justin . |
| 5,895,387 | 4/1999 | Guerrero et al. ......................... 606/71 |

OTHER PUBLICATIONS

ACE/Normed Bi–Directional and Multi–Directional Distractors for Craniomaxillofacial Callus Distraction. Catalog and General Operations. KLS Martin L.P., Jacksonville, FL, dated Jun. 1996.
Ilizarov GA; The principles of the Ilizarov method. Bull Hosp J Dis Orthop Inst 48:1–11, 1988.
Intraoral Distraction Device, acc. to Prof. M.–P. Vazquez–Dupré and Dr. P.A. Diner, Leibinger GmbH, Freiburg, Germany and Leibinger LP, Dallas, TX, copyright 1995.
Introducing Craniofacial Distractor and Mandibular Distractor, Developed by Romulo Guerrero, M.D., Quito, Equator, Wells Johnson Company, Tucson, AZ, undated.
Klein, C, Howaldt H–P: Correction of mandibular hypoplasia by means of bidirectional Callus distraction. *J Craniofacial Surg* 7:258–266, 1996.
McCarthy JG, Mandibular bone lengthening. *Oper Tech Plast Reconstr Surg* 1:99–104, 1994.
McCarthy JG, Schreiber JS, Karp NS, et al: Lengthening of the human mandible by gradual distraction. *Plast Reconstr Surg* 89:1–8, 1992.
McCarthy JG, Staffenberg DA, Wood RJ, et al: Introduction of an intraoral bone–lengthening device. *Plast Reconstr Surg* 96:978–981, 1995.
Original Hoffmann® Mini–Lengthening & External Fixation Device, Howmedica, Jacquet Orthopedie SA, Geneva, Switzerland, dated Nov. 1993.
Oritz–Monasterio F, Molina F: Mandibular distraction in hemifacial microsomia. *Oper Tech Plast Reconstr Surg* 1:105–112, 1994.
Snyder CC, Levine GA, Swanson HM, et al: Mandibular lengthening by gradual distration: preliminary report. *Plast Reconstr Surg* 51:506–508, 1973.
The Intraoral Distractor, acc. To Prof. Dr. M.–P. Vazquez and Dr. P.A. Diner, Leibinger, undated.
Yen, Stephen L–K: Distraction osteogensis: application to dentofacial orthopdics. *Sem Orthodontics* 3:257–283, 1997.

*Primary Examiner*—Michael Buiz
*Assistant Examiner*—Lien Ngo
*Attorney, Agent, or Firm*—Peacock, Myers & Adams; Stephen A. Slusher; Deborah A. Peacock

[57] ABSTRACT

Devices for lengthening bone, particularly the mandible and other small bones, by distraction osteogenesis are presented. The devices are implantable in an appropriate surgical procedure, and provide for an optional flexible drive shaft, used to transmit controlled torque for elongation of the devices thereby effecting distraction osteogenesis, which optional flexible drive shaft may conveniently terminate within the oral or buccal cavity. In one embodiment, the devices provide a telescoping screw assembly and drive means, which drive means may be an angled gear drive. In another embodiment, a threaded flexible drive shaft is provided which provides for elongation of the devices thereby effecting distraction osteogenesis.

36 Claims, 7 Drawing Sheets

APPARATUS FOR INTERNAL MANDIBULAR DISTRACTION

CROSS REFERENCE TO RELATED APPLICATIONS

This application is a continuation-in-part application of U.S. Provisional Patent Application Ser. No. 60/048,557, filed Jun. 4, 1997, entitled Apparatus for Internal Mandibular Distraction.

BACKGROUND OF THE INVENTION

1. Field of the Invention (Technical Field)

This invention relates to apparatuses for lengthening bones, primarily for the lengthening of the mandible by distraction osteogenesis.

2. Background Art

There are a variety of conditions characterized by asymmetric or unusually small mandibles. These include hemifacial microsomia, Treacher-Collins syndrome, lateral facial cleft, Pierre-Robin anomalies, post-traumatic growth asymmetries, and deformities resulting from traumatic injury. The incidence rate for hemifacial microsomia is approximately one in 5,000 births.

The preferred method for treatment is by distraction osteogenesis, in which a controlled fracture of the mandible is separated over a period of time, after the callus forms, allowing new bone to fill in the area of the stretched callus. Distraction osteogenesis of the human craniofacial skeleton enables the surgeon to gradually reposition abnormally formed bones of the face and jaw. The basic principles of distraction osteogenesis are that a surgical corticotomy or osteotomy is made and the two segments of bone are gradually moved apart at approximately 1 mm/day and then stabilized for bone consolidation.

To date, distraction of the mandible has been accomplished using external distraction devices, in which surgical pins are placed in the mandible on either side of the corticotomy or osteotomy, transiting the skin through the cheek, and a screw or rachet driven distraction device attached to the pins to provide distraction force. However, external devices for distraction which are currently available are bulky, and because of inherent limitations, have significantly limited the use of this surgical method. In the younger child and infant, which have relatively soft and small bones, conventional external distraction devices frequently cannot be utilized. In any patient treated using external distraction, significant scarring results from the surgical pins which transect the check, with tears and infection resulting from wound stretching in the gradual separation of the bisected jaw. In addition, external distraction lacks adequate control, in part because distraction frequently flexes the pins or causes the pins to migrate through the bone; is readily subject to dislocation, particularly with younger patients; and has a socially unacceptable appearance, giving rise to poor patient compliance.

Distraction osteogenesis has substantial advantages over other methods of mandibular surgical advancement. This technique can produce unlimited quantities of living bone which can be formed along any plane of space. Because distraction osteogenesis uses local host tissue, it offers many advantages over bone grafting. Expansion of the entire functional matrix of the mandible is achieved, so that the muscle, nerves and skin are maintained intact. Distraction osteogenesis is less invasive than conventional craniofacial surgery; while the bones must be cut using either technique, with distraction they are not forcibly broken, and thus blood loss and postoperative swelling are lessened.

Distraction osteogenesis has a long history in limb lengthening and was popularized by the Soviet orthopedic surgeon, Ilizarov in the 1950's (Ilizarov G A: The principles of the Ilizarov method. *Bull Hosp J Dis Orthop Inst* 48:1, 1988). He developed the technique of distraction osteogenesis for gradual lengthening of the long bones to treat many congenital and acquired deformities. Distraction was first applied to the membranous facial bones by Snyder, who successfully lengthened canine mandibles with external devices (Snyder C C, Levine G A, Swanson H M, et al: Mandibular lengthening by gradual distraction: preliminary report. *Plast Reconstr Surg* 51:506, 1973). From numerous animal experiments, a large body of information has accumulated which details the efficacy of distraction osteogenesis in the craniofacial skeleton. In 1992, McCarthy reported on four children with craniofacial microsomia and Nagar's syndrome who underwent successful mandibular distraction with an external device (McCarthy J G, Schreiber J S, Karp N S, et al: Lengthening of the human mandible by gradual distraction. *Plast Reconstr Surg* 89:1, 1992). In 1994, McCarthy and Ortiz-Monasterio each reported their own successful experiences with mandibular distraction (McCarthy J G, Mandibular bone lengthening. *Oper Tech Plast Reconstr Surg* 1:99–104, 1994; Oritz-Monasterio F, Molina F: Mandibular distraction in hemifacial microsomia. *Oper Tech Plast Reconstr Surg* 1:105–112, 1994). Only recently have limited human studies been conducted utilizing a bidirectional external distractor (Klein C, Howaldt H -P: Correction of mandibular hypoplasia by means of bidirectional callus distraction. *J Craniofacial Surg* 7:258–266, 1996). Using external devices, there appears to be long-term improvement of mandibular morphology with minimal complications.

The most widely used prior art mandibular distraction device is unidirectional. In mandibular deformities such as hemifacial microsomia and Treacher Collins syndrome, both vertical and horizontal bone lengthening are required to correct facial asymmetries or deficient vertical facial heights. The surgical solutions utilizing distraction osteogenesis are limited by the available distraction devices. If an unidirectional distraction device is used, then the available bone and developing tooth buds tend to dictate the direction of the osteotomy cuts, the position of the fixation pins and ultimately, the vector of bone regeneration. Several surgeons have reported the use of bidirectional distractors and a two-cut approach to achieve two-dimensional control of three mandibular segments. All of these bidirectional devices are external and share the same undesirable cosmetic problems associated with other external distractors.

The advantages of an implanted device are both therapeutic and cosmetic, including less danger of dislocation by falls or bumping, greater distraction control, and no external scarring. An implantable device can also be adapted for other types of reconstruction in craniofacial surgery such as maxillary expansion, maxillary advancements, symphyseal widening and monoblock facial advancements.

SUMMARY OF THE INVENTION

DISCLOSURE OF THE INVENTION

The present invention is directed to implanted devices for use in facial surgery, primarily for correction of congenital abnormalities of the jaw, such as maxillary hypoplasia, and reconstructive maxillo-facial surgery which requires growth of bone tissue. A surgical corticotomy, osteotomy or similar procedure is performed, such that the bone is cut at the location where extension is desired, preferably leaving internal nerves intact, and the device is then mounted such that it traverses the locus of the bone cut, and is securely anchored to the bone, through pins, screws, surgical adhesive or other means, to both the proximal and distal sides of the bone cut. Through successive, gradual adjustment to the device, resulting in distraction in the area between the proximal and distal sides of the bone cut, growth and repair of bone tissue across an area of bone cut may be both directed and enhanced.

In the preferred embodiment of the present invention, a device is provided for lengthening bone by distraction osteogenesis which includes a telescoping screw assembly with at least two members, a first member threaded shaft cooperatively engaged with the inner screw thread of opposite thread hands of a second member tubular screw having an outer screw thread and an inner screw thread of opposite thread hands; a nut fixed in rotation for engaging the outer screw thread of the second member tubular screw and forming a part of first securing means for securing to the bone; and an angled drive means for providing a drive force to the telescoping screw assembly and in communication with the first member threaded shaft and forming a part of second securing means for securing to the bone. In this device, the telescoping screw assembly optionally includes one or more additional members consisting of a tubular screw having an outer screw thread and an inner screw thread of opposite thread hands and threadably engaged and disposed between the first member threaded shaft and the second member tubular screw. The first securing means may be a plate which includes means for fastening to bone. The first securing means may also include engagement means for removably attaching the nut to the plate, with the plate including an engagable assembly, such that the plate may be secured to the bone prior to attaching the nut to the plate, and such that the nut may be subsequently unattached from the plate. The plate may be a bioresorbable plate, and the plate may also be attached to the bone by use of bioresorbable surgical fasteners. The angled drive means of the device may be an angled gear drive, including a reducing gear drive, and the angled gear drive may be a worm, helical, bevel or hypoid gear drive. The angled drive means may be at least partially contained within a housing, which housing also includes the second securing means for securing to the bone, such as a plate. The device may also include a tongue, slidably engaged to the first securing means and the second securing means through a slot provided therefore in the first securing means and second securing means, so that rotation of the first securing means relative to the second securing means is prevented.

In an alternative embodiment of the present invention, a device for lengthening bone by distraction osteogenesis is provided with a first telescoping screw assembly made up of at least two members, a first member threaded shaft cooperatively engaged with the inner screw thread of opposite thread hands of a second member tubular screw having an outer screw thread and an inner screw thread of opposite thread hands, a second telescoping screw assembly comprising at least two members, a first member threaded shaft cooperatively engaged with the inner screw thread of opposite thread hands of a second member tubular screw having an outer screw thread and an inner screw thread of opposite thread hands, a first nut assembly fixed in rotation for engaging the outer screw thread of the second member tubular screw of the first telescoping screw assembly and forming a part of the first securing means for securing to the bone, a second nut assembly fixed in rotation for engaging the outer screw thread of the second member tubular screw of the second telescoping screw assembly and forming a part of the second securing means for securing to the bone and an angled drive means for providing a drive force to the first and second telescoping screw assemblies and in communication with the first member threaded shaft of each of the first and second telescoping screw assemblies. In this device, either the first or the second telescoping screw assemblies, or both, may include one or more additional members consisting of a tubular screw having an outer screw thread and an inner screw thread of opposite thread hands and threadably engaged and disposed between the first member threaded shaft and the second member tubular screw. The first securing means and second securing means may be a plate and means for fastening the plate to the bone. The angled drive means may be an angled gear drive, such as a worm, helical, bevel or hypoid gear drive. The angled drive means may be at least partially contained within a housing, which housing includes third securing means, such as a plate, for securing the housing to the bone.

In an alternative device of the present invention for lengthening bone by distraction osteogenesis, there is provided a telescoping screw assembly comprising at least two members, a first member threaded shaft cooperatively engaged with the inner screw thread of opposite thread hands of a second member tubular screw having an outer screw thread and an inner screw thread of opposite thread hands, a nut fixed in rotation for engaging the outer screw thread of the second member tubular screw and forming a part of first securing means for securing to the bone and drive means for providing a drive force to the telescoping screw assembly and in communication with the first member threaded shaft and forming a part of second securing means for securing to the bone. The telescoping screw assembly may optionally include one or more additional members consisting of a tubular screw having an outer screw thread and an inner screw thread of opposite thread hands and threadably engaged and disposed between the first member threaded shaft and the second member tubular screw. The first securing means may be a plate with means for fastening to bone. The first securing means may also include engagement means for removably attaching the nut to the plate, where the plate includes an engagable assembly, so that the plate and engagable assembly may be secured to the bone prior to attaching the nut to the plate, and so that the nut may be subsequently unattached from the plate. The plate may be a bioresorbable plate, and may be attached to the bone by use of bioresorbable surgical fasteners. The drive means may include a flexible shaft in communication with the first member threaded shaft and partially contained within a housing, which housing includes a plate which is part of the second securing means for securing to the bone. The device may also include a tongue, slidably engaged to the first securing means and the second securing means through a slot provided therefore in the first securing means and second securing means, so that rotation of the first securing means relative to the second securing means is prevented.

In an alternative embodiment of the present invention, there is also provided a device for lengthening bone by distraction osteogenesis composed of at least two members, a first member tubular screw having a first end and a second end and an outer screw thread and an inner screw thread of opposite thread, which inner screw thread is cooperatively engaged with threads of opposite thread hands of a second member threaded shaft, a nut for engaging the outer screw thread of the first member tubular screw connected to and fixed in position relative to a first securing means for securing to the bone, a drive means for providing a drive force to the telescoping screw assembly and in communication with the first end of the first member tubular threaded shaft, and a second securing means for securing to the bone, the second member threaded shaft being fixed to the second securing means. The first securing means may include a plate with means for fastening to bone, and may also include engagement means for removably attaching the nut to the plate, so that the plate includes an engagable assembly so that the plate comprising an engagable assembly may be secured to the bone prior to attaching the nut to the plate, and so that the nut may be subsequently unattached from the plate. The plate may be a bioresorbable plate, and may be attached to the bone by use of bioresorbable surgical fasteners. The drive means may include a flexible shaft in communication with the first end of the first member threaded shaft and partially contained within a housing, which housing includes a plate for securing to the bone. This device may also include a tongue, slidably engaged to the first securing means and the second securing means through a slot provided therefore in the first securing means and second securing means, whereby rotation of the first securing means relative to the second securing means is prevented.

In an alternative embodiment of the present invention, a device for lengthening bone by distraction osteogenesis is provided with a threaded flexible drive shaft having a first end and a second end, a nut fixed in rotation for engaging the screw thread of the threaded flexible drive shaft and forming a part of first securing means for securing to the bone and second securing means for rotatably engaging the second end of the threaded flexible drive shaft and securing it to be the bone. The first securing means may be a plate with means for fastening to bone. The first securing means may also include engagement means for removably attaching the nut to the plate, the plate including an engagable assembly, so that the plate with an engagable assembly may be secured to the bone prior to attaching the nut to the plate, and so that the nut may be subsequently unattached from the plate. The plate may be a bioresorbable plate, and may be attached to the bone by use of bioresorbable surgical fasteners. The device may also include a tongue, slidably engaged to the first securing means and the second securing means through a slot provided therefore in the first securing means and second securing means, so that angular displacement of the first securing means relative to the second securing means is prevented. Alternatively, the device may include a plurality of nested telescoping tubes with the threaded flexible drive shaft lying within the nest telescoping tubes, the nested telescoping tubes being disposed between the first securing means and the second securing means, so that angular displacement of the first securing means relative to the second securing means is prevented.

In all embodiments, anchoring to the jaw can be accommodated by seatings at either end for standard surgical pins or surgical screws, including standard 2.0 or 1.5 mm surgical screws.

The devices may employ a flexible shaft exiting through an incision in the cheek within the oral cavity or buccal cavity, affording intra-oral access for a wrench to rotate a screw or driver located at the proximal end of the flexible drive shaft. In any event, the devices may be implanted sub-mucosally.

Screw actuation occurs at a rate determined by the physician through means of the patient or care giver engaging a wrench with a drive, such as a recessed socket-head drive. The socket-head drive may communicate with the implanted device via a flexible shaft. In one embodiment, one full rotation of the wrench corresponds to approximately 0.5 mm lengthening of the device. In another embodiment, the device provides a flexible shaft through which torque is applied, through a terminal socket head fitting and manual wrench or similar means, with the torque of the flexible shaft transferred to a screw-actuated unit which provides distraction. The screw-actuated unit may be an in-line drive, a right-angle drive, or any angled drive at any appropriate angle to the distal end of the flexible shaft. The flexible shaft adjusting means is enclosed by sheath, exits the skin through the oral mucosa, and is placed so that the flexible shaft is largely or entirely within the oral cavity. The sheath prevents rubbing and friction against the mucosa when the shaft is rotated, and permits formation of a static seal around the sheath and a dynamic seal around the flexible shaft. The stability of the shaft and sheath ensures that the mucosal tissue is isolated from forces applied to the screw-actuator by the wrench. The flexible shaft permits the device to be oriented in the direction determined by the surgeon in order to properly direct bone growth, while the flexible shaft can be aimed toward the front of the mouth for ease of turning. Alternatively, the flexible shaft can exit through the skin behind the jaw, adjacent to the ear, or in another location determined by the surgeon to be appropriate for the distraction desired. The length of the flexible shaft can be varied by inserting a lengthening or extension screw of appropriate length to the flexible shaft, and trimming the covering sheath, if provided, to the appropriate length, thereby allowing the screw-actuator to be optimally positioned within the oral cavity for ease of use in rotation. The covering sheath may, but need not, be partially enclosed within a rigid or semi-rigid bendable tube, slotted tube, bellows-type tube or a similar tube, made out of metal, medical grade plastics or a similar suitable material, thereby more firmly isolating the mucosa from the torque of the flexible shaft. The covering sheath or the tube may optionally further be stabilized by anchoring to one or more teeth, thereby more firmly isolating the mucosa from the torque of the flexible shaft.

With devices employing a flexible shaft, once the desired distraction is obtained, generally a period of one to four weeks, the adjustment nut, shaft and sheath can be removed. During the period of bone consolidation, generally two to four months, the entire device is implanted, with no external aspect. Upon satisfactory bone consolidation, the internal device can then be surgically removed.

In another aspect of the invention, lengthening screws may be successively added, using the sheath as a conduit, to permit additional distraction without the requirement for additional surgery. This minimizes the size of the initial implanted unit while maximizing the potential length of distraction.

The flexible drive shaft sheath can be formed in situ to a shape optimizing patient comfort and hex key access, and can be a bendable tube, a slotted tube, a bellows-type tube or a similar tube, made out of metal, medical grade plastics or a similar suitable material.

The devices of the invention may optionally employ a compression spring, or similar means for the translation of force, within the drive mechanism. Without elasticity, the device translates rotations of the input drive shaft directly into increased bone gap. Thus the bone lengthening process occurs in a pulsing pattern, with an incremental jump occurring at the time the input drive shaft is rotated. By inserting a spring of appropriate stiffness, the displacement introduced by the rotation of the drive shaft is primarily converted to an initial displacement or compression of the spring. The spring then exerts a steady spreading force upon the two bone segments, causing them to spread slowly apart in a continuous manner over the interval of time between adjustments. Some research suggests that a more continuous distraction produces higher quality bone in a shorter period of time than intermittent distraction, and may produce the desired distraction with less force than that required with intermittent distraction.

In another aspect of the invention, a device is provided for use in surgical procedures wherein bidirectional distraction of the mandible is desired, and where two cuts of the mandible are made. In this device, two drive units, a proximal and distal drive unit, each with a telescoping screw drive, are provided, each with a flexible drive shaft which may be enclosed within a sheath. With two cuts of the mandible, the device is anchored through three screws, pins or other means, such that the proximal end is anchored on the proximal side of the first cut, the middle of the device is anchored to the bone fragment created by the two cuts, and the distal end is anchored on the distal side of the second cut. The middle anchor may be on a pivot, or may be fixed. The relative amount of horizontal and vertical distraction may be controlled by specifying the number of rotations to be applied to each of the proximal and distal drive units, such that relatively more horizontal distraction than vertical distraction, or vice versa, may be obtained. The relative amount of horizontal and vertical distraction may also be controlled by varying the angle between the proximal and distal drive units, which angle may be adjustable.

In another aspect of the invention, a reduction gear is employed, which may be an angled worm, helical, hypoid or bevel gear, forming a right angle or any angle desired, for translating the torque upon rotation of the flexible shaft to the screw drive, which optionally may be a telescoping screw drive, which separates the proximal and distal ends of the device, thereby providing distraction. The pitch of the threads, diameter of gear and the like may be varied to obtain the degree of reduction desired. By use of a reduction drive, sufficient force may be developed by the device to complete the fracture of the mandible, in the event of less than a complete fracture, and initiate the distraction process.

In another aspect of the invention, the flexible shaft communicates with a gear housing, wherein a drive communicates with two screw drives, one providing anterior distraction, and the other providing posterior distraction, so that a rotation of the flexible shaft simultaneous communicates with both screw drives.

In another aspect of the invention, a guide or template for distraction is provided, such that a device with a single drive unit will follow a "track" on extension, so that the device provides distraction in both the vertical and horizontal directions with a single cut of the bone, and bone growth may be directed along a curved arc. In one aspect, the drive unit is anchored to the bone on the proximal side of a bone cut and movably communicates with a rigid and preformed guide rail or wire, and a drive plate, which also movably communicates with the rigid and preformed guide rail or wire, is anchored to the bone on the distal side of the bone cut. In related aspects of the invention, either the drive unit or the drive plate may be fixed to the rigid and preformed guide rail or wire. In yet another aspect of the invention, the guide rail or wire may be shaped or formed prior to surgery, based upon characteristics of the patient's mandible and the desired results, to obtain the desired distraction.

In another aspect of the invention, a keyhole-type engagement, optionally with a detente to securely seat the screw or pin, is employed at both the proximal and distal screw locations, or alternatively at only one location. This permits accurate location of the device, and assists in insertion and subsequent removal of device. Similarly, an angled slot engagement for receiving a screw or pin may be employed, optionally also with a detente or other seating means to securely seat the screw or pin.

In another aspect of the invention, a separate attachment plate is provided, for attaching the distractor device to the bone, at the proximal or distal locations of the device, or both, wherein the attachment plate or plates are attached to the bone, by screws or other means known in the art, and an interconnecting means is provided, whereby the distractor device can be connected to the attachment plates, and preferably so that the distractor device may be easily removed following distraction and consolidation of the bone.

In another aspect of the invention, a screw template is provided, with openings corresponding to the desired placement of surgical screws or pins on the distal and proximal ends of the device, such that the template can be used by the surgeon to place the surgical screws or pins, following which the template is removed, leaving the surgical screws or pins in place. The distraction device, which may employ a keyhole-type engagement or angled slot-type engagement at either or both the distal and proximal ends of the device, is then placed such that the screws or pins transit the keyhole, or in the case of an angled slot are within the angled slot, and torque applied through the flexible drive shaft as necessary to extend the device to securely seat it, optionally with a locking detente or other seating means to securely seat and lock the screws or pins.

In another aspect of the invention, a fully internal implantable device is provided which contains a drive engine which incorporates a motor utilizing electric, chemical or other motive means, including shape memory alloy means. The drive engine may be externally controlled, such as through radio frequency or ultrasonic means. The drive engine may incorporate a remotely charged power supply. The drive engine may be such that comparatively low forces applied continuously are utilized for distraction, rather than relatively high and intermittent forces.

In another aspect of the invention, a stored energy drive device may be employed, such as through use of compressed gas means, compressed fluid means, preloaded spring means or other stored energy means, and which stored energy is released in discrete units by rotation of a flexible shaft, depression or extension of a flexible shaft, a timer, including electric timer, electromagnetic means or other actuation means.

In yet another aspect of the invention, remotely monitorable force and displacement sensors are provided, which may be incorporated into the distraction device, to provide a measurement of the force required for distraction and to measure osteogenesis. These sensors communicate by radio frequency, ultrasonic or other means, such that measurement information can be obtained by the physician. Information obtained from force and displacement sensors can be utilized to adjust the rate or direction of distraction and to determine when to cease the distraction process.

The implantable devices of the present invention may be employed for procedures other than mandibular distraction, and can generally be employed in any procedure in which distraction of small bones is desired. The devices can also be employed, with such adaptations as are necessary, for other types of craniofacial surgery, such as maxillary expansion, maxillary advancements, symphyseal widening and monoblock facial advancements, as well as distraction of small bones, such as bones of the wrist, hand, ankle and foot.

Other objects, advantages and novel features, and further scope of applicability of the present invention will be set forth in part in the detailed description to follow, and in part will become apparent to those skilled in the art upon examination of the following, or may be learned by practice of the invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE PREFERRED EMBODIMENT

In the general procedure for utilizing the devices of the present invention for distraction of the mandible, under general anesthesia an approximately 3 cm incision is made on the lateral mandibular vestibulum near the gonium, including the mucosa and periosteum. The periosteum is undermined, exposing the gonium, part of the ascending ramus, and part of the mandibular body. Using a drill, a corticotomy is made on the external side of the mandible. It is extended around the anterior and posterior mandibular border through the area of the maximum bone thickness. The internal cortical layer and nerves are not exposed. Alternatively, an osteotomy is made. The site for placement of the surgical screws or other attachment means anchoring the distraction device is then decided. The position of the screws or other attachment means in the mandible necessarily affects the vector of distraction forces, and the relative amount of horizontal and vertical distraction. In many cases, the screws or other attachment means can be placed such that the distractor is oblique, and roughly parallel to normal ascending ramus.

The devices are surgically implanted as described and, after stabilization for a period, preferably approximately one week, the devices are used for distraction for a period from about two to about four weeks or more, preferably at a nominal rate of distraction of approximately 1 mm/day. Following distraction to the desired length, the devices are left in situ during bone healing, preferably for about two to about four months. During the bone healing period, the flexible drive shaft, if provided, may optionally be removed. Following consolidation of the bone, the device can then be surgically removed.

Figure 1A:
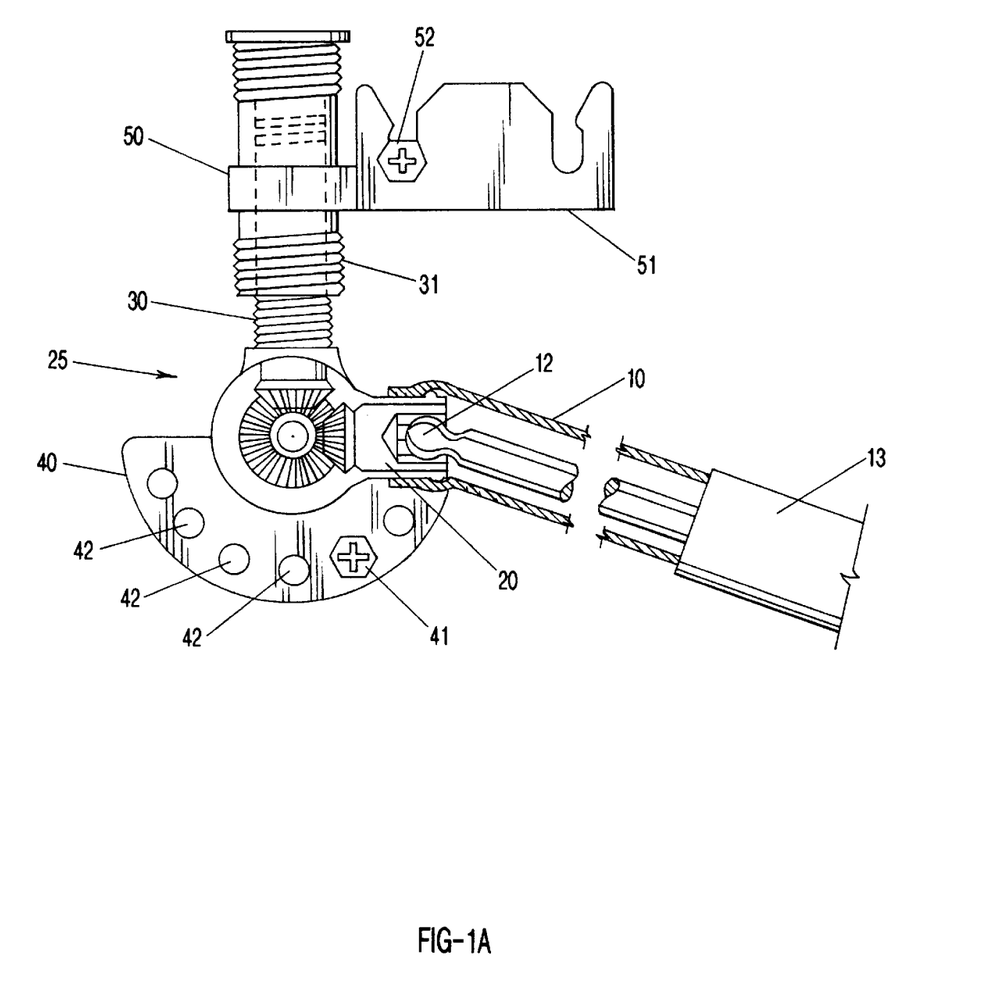
FIGS. 1A, 1B and 1C are top and side views of the preferred embodiment of an apparatus of the present invention for lengthening bones incorporating a flexible input shaft, bevel gear drive and telescoping screw drive.
Figure 1B:
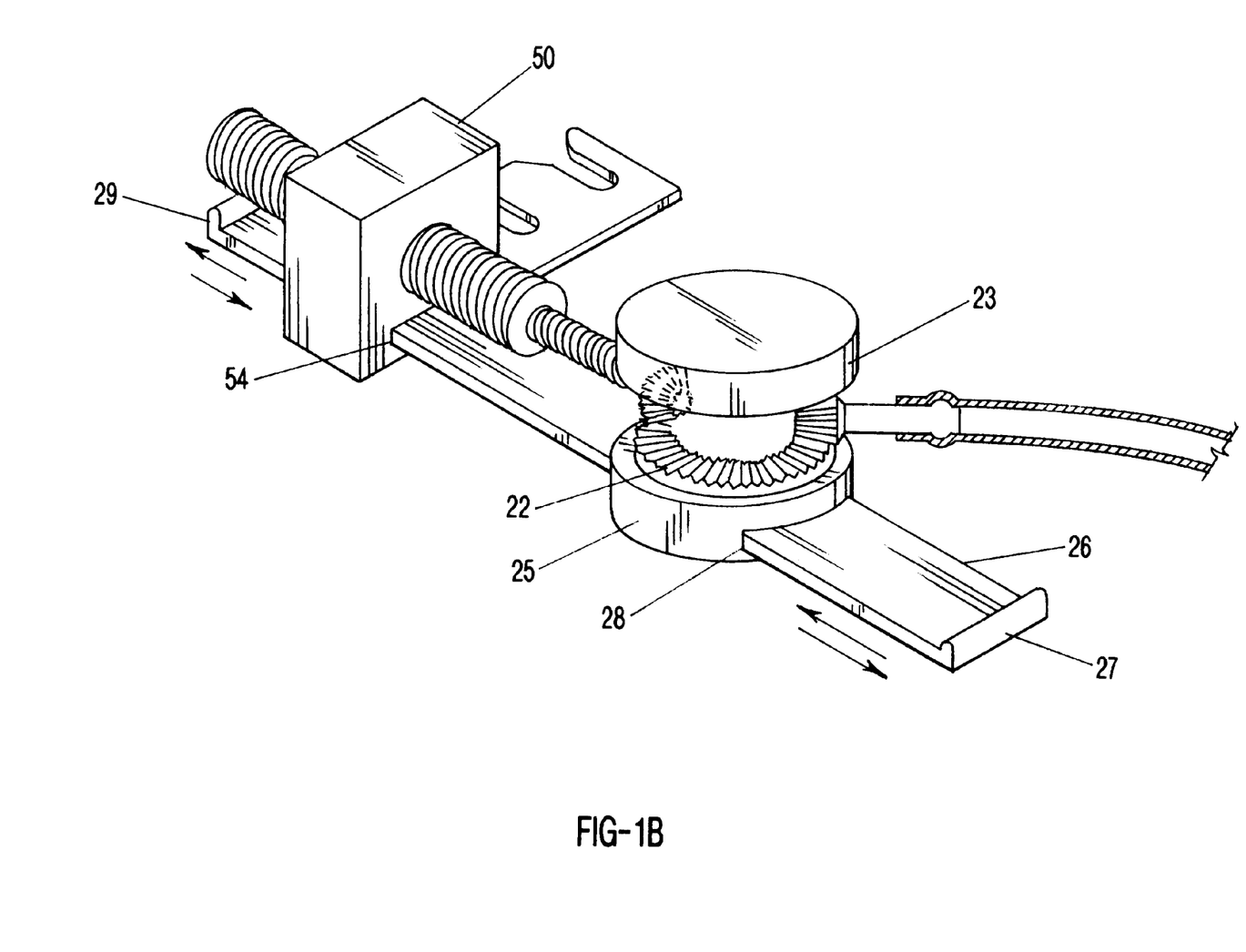
Figure 1C:
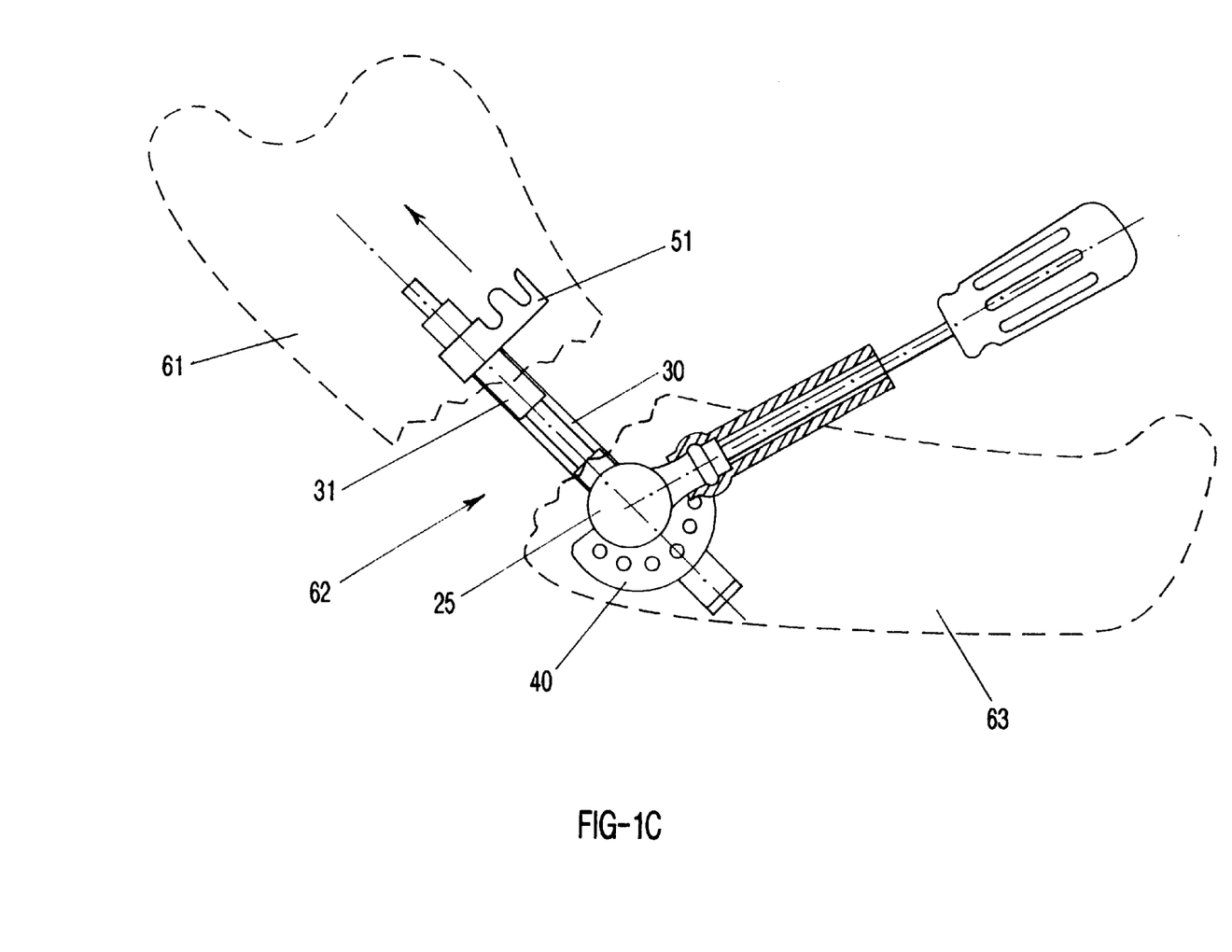

The preferred embodiment shown in FIG. 1 is configured as a self-contained unit to provide for distraction of the jaw by means of screw-actuated extension of its length utilizing a bevel gear drive. FIG. 1A shows sheath 10, which may be made of any tubing material, including preformed metal tubing or a plastic or composite medical grade tubing. In use of this device for distraction osteogenesis of the mandible, sheath 10 exits through the cheek within the oral or buccal cavity, and may be accessed therein utilizing hex driver 13 or other similar driver means, which may also be a flexible shaft. Hex driver 13 terminates in hex head 12, which upon insertion of hex driver 13 into sheath 10 engages hex receiving unit 20, which unit also communicates with and comprises a portion of bevel drive unit 25. Bevel drive unit 25 is in turn attached to base anchor plate 40, which base anchor plate 40 contains a plurality of holes 42. In use, base anchor plate 40 is attached to the bone forming a part of the mandible, or other bone to be distracted, by use of anchor screws 41 inserted through holes 42, it being understood that other anchor means may be employed, including surgical pins or nails and screws with hexagonal or other drive bolt heads. Bevel drive unit 25 in turn communicates with first telescopic drive shaft 30, which in turn communicates with the internally threaded portion of second telescopic tubular drive shaft 31, which second telescopic tubular drive shaft 31 is both internally and externally threaded. Second telescopic tubular drive shaft 31 in turn communicates with drive anchor plate nut 50, which drive anchor plate nut 50 is attached to drive anchor plate 51. Drive anchor plate 51 is, in use, attached to the bone forming a part of the mandible, or other bone to be distracted, by use of anchor screws 52, it being understood that other anchor means may be employed, including surgical pins or nails and screws with hexagonal or other drive bolt heads. The site of the corticotomy or osteotomy lies between base anchor plate 40 and drive anchor plate 51, thereby defining two bone segments. Upon rotation of hex driver 13 hex receiving unit 20 is rotated, which rotation is communicated to first telescopic drive shaft 30, which in turn communicates with the internally threaded portion of second telescopic tubular drive shaft 31, and which in turn communicates with drive anchor plate nut 50, such that telescopic drive shafts 30 and 31 extend, causing the distance between base anchor plate 40 and drive anchor plate 51 to increase, thereby distracting or separating the bone segments.

FIG. 1B illustrates additional features of the device of FIG. 1, including crown gears 22 and 23 forming a part of bevel drive unit 25. In this embodiment, a tongue 26 is provided, terminating in a proximal lip 27 and distal lip 29, and which transits bevel drive unit 25 through means of bevel drive unit slot 28 and transits drive anchor plate nut 50 through means of drive anchor plate slot 54, such that tongue 26 prevents rotation of drive anchor plate nut 50 relative to bevel drive unit 25, it being understood that, as depicted, tongue 26 is slidably engaged via slots 28 and 54 to drive anchor plate nut 50 and bevel drive unit 25, and is thereby not fixed to either drive anchor plate nut 50 or bevel drive unit 25. Not depicted in FIG. 1B is the base anchor plate attached to bevel drive unit 25. In alternative configurations in which a tongue is employed, it is understood that the tongue might be fixed to either anchor plate nut 50 or bevel drive unit 25, and slidably engaged to the remaining member of the pair.

FIG. 1C depicts the device of FIG. 1 attached to bone, with drive anchor plate 51 affixed to a portion of ramus 61, with telescopic drive shafts 30 and 31 bridging the situs of distraction 62 formed by the surgical corticotomy or osteotomy, and with base anchor plate 40 affixed to a portion of mandible 63, such that in operation situs of distraction 62 is increased on an incremental basis, thereby permitting the growth of additional bone.

Figure 2:
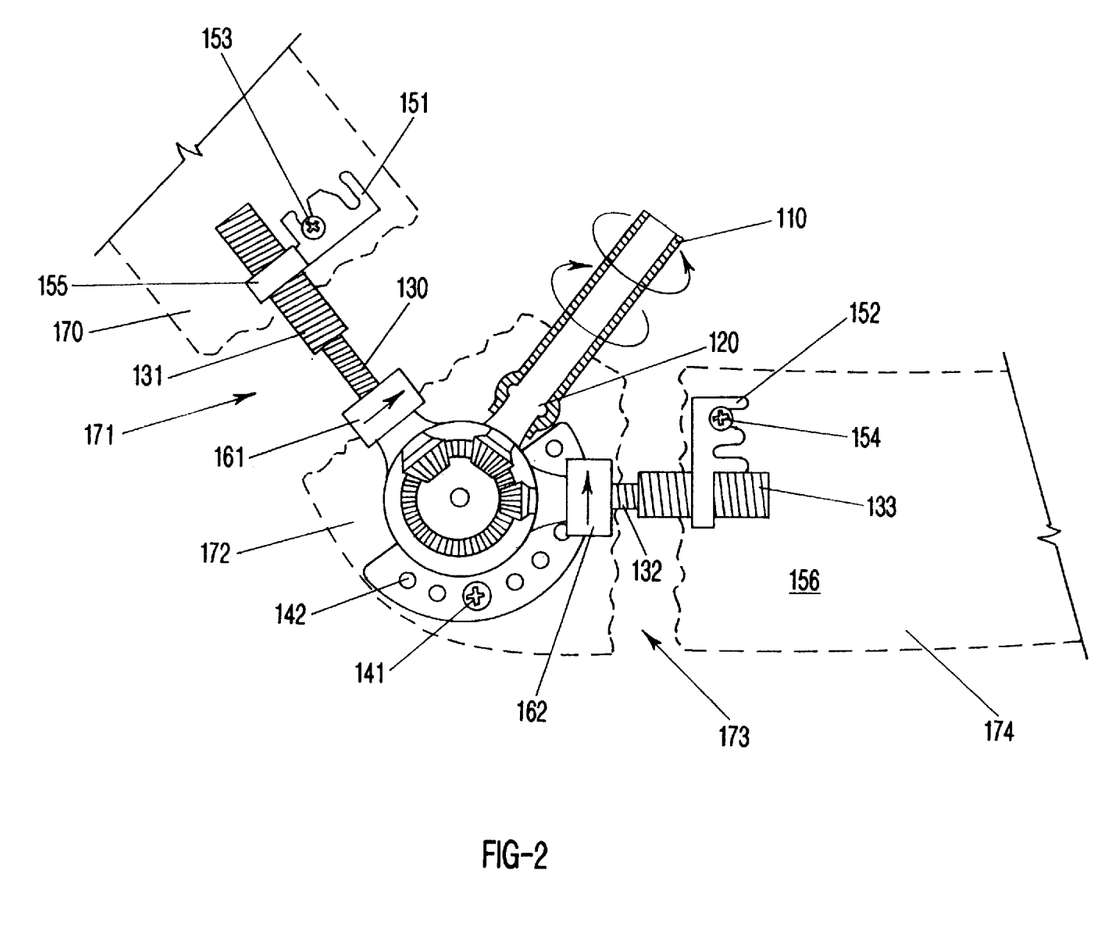
FIG. 2 is a top view of an alternative embodiment of an apparatus of the present invention for lengthening bones incorporating a flexible input shaft, bevel gear drive and two telescoping screw drives with one-way clutch mechanisms.

The alternative embodiment shown in FIG. 2 is a self-contained unit to provide for distraction of the jaw by means of two distinct screw-actuated extensions of its length utilizing a bevel gear drive. FIG. 2 shows sheath 110, which may be made of any tubing material, including preformed metal tubing or a plastic or composite medical grade tubing. In use of this device for distraction osteogenesis of the mandible, sheath 110 exits through the cheek within the oral or buccal cavity, and may be accessed therein utilizing a hex driver or other similar driver means, which driver means may include a flexible shaft. The hex driver terminates in a hex head, which upon insertion of the hex driver into sheath 110 engages hex receiving unit 120, which unit also communicates with and comprises a portion of bevel drive unit 125. Bevel drive unit 125 is in turn attached to base anchor plate 140, which base anchor plate 140 contains a plurality of holes 142. In use, base anchor plate 140 is attached to the bone forming a part of the mandible, or other bone to be distracted, by use of anchor screws 141 inserted through holes 142, it being understood that other anchor means may be employed, including surgical pins or nails and screws with hexagonal or other drive bolt heads. Bevel drive unit 125 in turn communicates with two distinct telescopic drive shafts, proximal first telescopic drive shaft 132 and distal first telescopic drive shaft 130. Proximal first telescopic drive shaft 132 in turn communicates with the internally threaded portion of proximal second telescopic tubular drive shaft 133, which proximal second telescopic tubular drive shaft 133 is both internally and externally threaded. Proximal second telescopic tubular drive shaft 133 in turn communicates with proximal drive anchor plate nut 156, which proximal drive anchor plate nut 156 is attached to drive anchor plate 152. Drive anchor plate 152 is, in use, attached to the bone forming a part of the mandible, or other bone to be distracted, by use of anchor screws 154, it being understood that other anchor means may be employed, including surgical pins or nails and screws with hexagonal or other drive bolt heads. Distal first telescopic drive shaft 130 similarly communicates with the internally threaded portion of distal second telescopic tubular drive shaft 131, which distal second telescopic tubular drive shaft 131 is both internally and externally threaded. Distal second telescopic tubular drive shaft 131 in turn communicates with distal drive anchor plate nut 155, which distal drive anchor plate nut 155 is attached to drive anchor plate 151. Drive anchor plate 151 is, in use, attached to the bone forming a part of the mandible, or other bone to be distracted, by use of anchor screws 153, it being understood that other anchor means may be employed, including surgical pins or nails and screws with hexagonal or other drive bolt heads. Two one-way clutches are provided, proximal one-way clutch 162 and distal one-way clutch 161, such that upon rotation of hex receiving unit 120 in one direction one clutch is engaged and one clutch disengaged, and upon rotation of hex receiving unit 120 in the opposite direction, the opposite obtains. Thus, in use, upon rotation of hex receiving unit 120 in a clockwise direction, torque would be transmitted through distal one-way clutch 161, wherein left handed threads employed on distal telescoping screws 130 and 131 would cause extension of the distal telescoping screws 130 and 131, while no torque would be transmitted through proximal one-way clutch 162. Similarly, upon rotation of hex receiving unit 120 in a counter-clockwise direction, torque would be transmitted through proximal one-way clutch 162, wherein right handed threads employed on proximal telescoping screws 132 and 133 would cause extension of the proximal telescoping screws 132 and 133, while no torque would be transmitted through distal one-way clutch 161. In use of this device, distal drive anchor plate 155 is affixed to a portion of descending ramus 170, with distal telescopic drive shafts 130 and 131 bridging the situs of first distraction 171 formed by surgical corticotomy or osteotomy, base anchor plate 140 is affixed to a floating portion of first mandible 172, and proximal drive anchor plate 152 is affixed to a portion of second mandible 174, with proximal telescopic drive shafts 132 and 133 bridging the situs of second distraction 173 formed by surgical corticotomy or osteotomy, such that in operation the situs of first distraction 171, which is primarily vertical in orientation, can be increased on an incremental basis by rotation of hex receiving unit 120 in one direction, and the situs of second distraction 173, which is primarily horizontal in orientation, can be increased on an incremental basis by rotation of hex receiving unit 120 in the opposite direction. In this way, the amount of vertical and horizontal lengthening of the mandible can be independently controlled.

Figure 3:
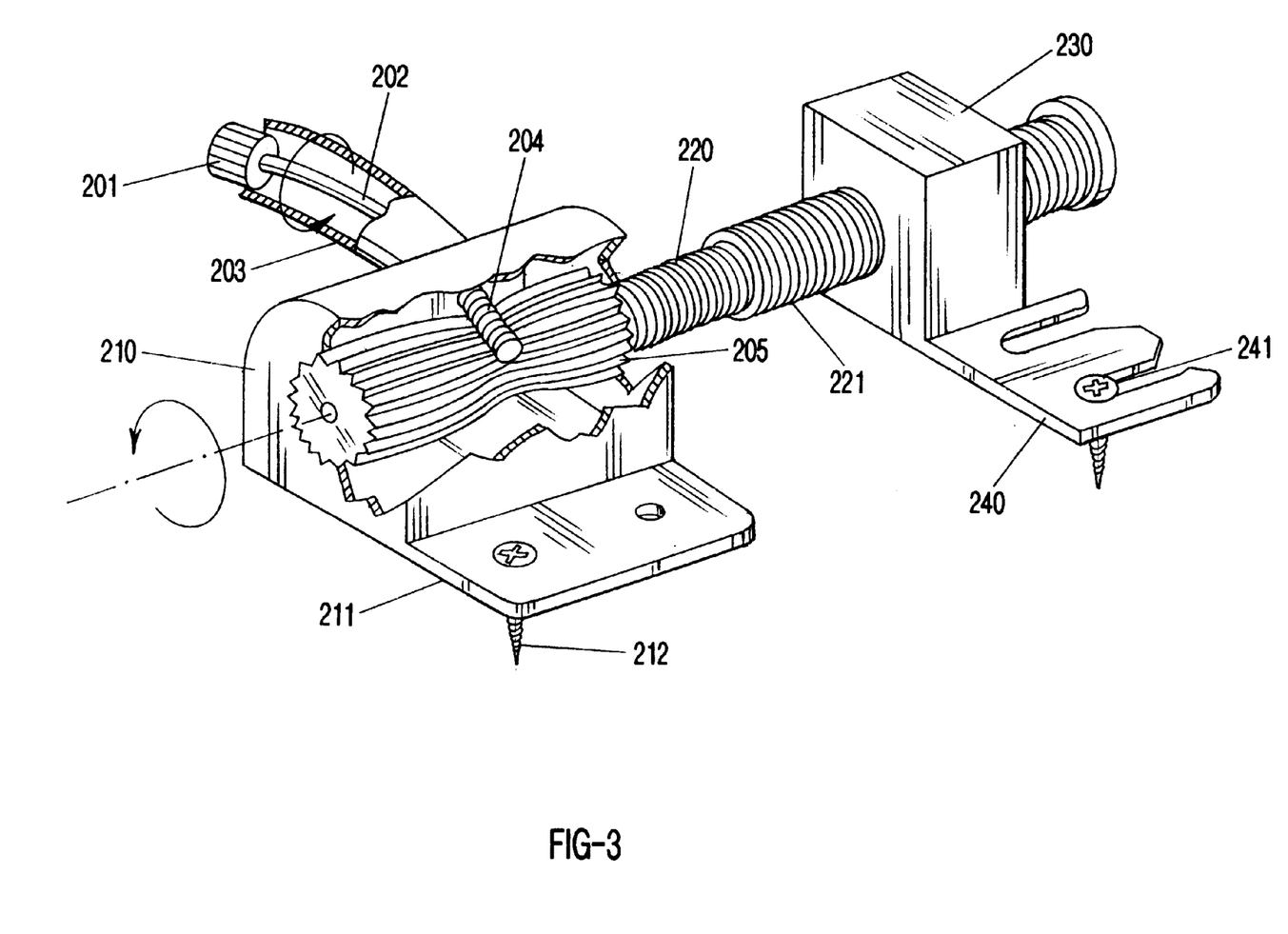
FIG. 3 is a side view of an alternative embodiment of an apparatus of the present invention for lengthening bones incorporating a flexible input shaft, right angle worm drive and telescoping screw drive.

FIG. 3 illustrates an alternative embodiment with flexible shaft 202, which flexible shaft 202 is contained within sheath 203, which sheath 203 may be made of any tubing material, including preformed metal tubing or a plastic or composite medical grade tubing. In use of this device for distraction osteogenesis of the mandible, sheath 203 containing flexible shaft 202 exits through the cheek within the oral or buccal cavity, and may be accessed therein utilizing a hex driver or other similar driver means, which hex driver engages socket head drive 201 attached to flexible shaft 202. The distal end of flexible shaft 202 terminates in worm gear 204. In use, flexible shaft 202 is rotated by engaging socket head drive 201 with a hexagonal wrench, driver or similar device. Flexible shaft 202 and worm gear 204 terminate in gear housing 210, it being understood that gear housing 210 may be any shape desired, wherein is contained an angled gear drive. In some embodiments of the device, the angle gear drive may be a reducing gear drive, and may further be a worm, helical, hypoid or bevel gear drive, either right angle or any angle desired or provided. Gear housing 210 is in turn attached to base anchor plate 211, which base anchor plate 211 contains a plurality of holes. In use, base anchor plate 211 is attached to the bone forming a part of the mandible, or other bone to be distracted, by use of anchor screws 212 inserted through the holes, slots or other receiving means provided, it being understood that other anchor means may be employed, including surgical pins or nails and screws with hexagonal or other drive bolt heads. Worm gear 204 is engaged with wheel gear 205, such that on rotation of worm gear 204 wheel gear 205 also rotates. Wheel gear 205 forms a part of first telescopic drive shaft 220, which in turn communicated with second telescopic tubular drive shaft 221, which second telescopic tubular drive shaft 221 is both internally and externally threaded. First telescopic drive shaft 220 and second telescopic tubular drive shaft 221 are threaded such that upon rotation of flexible shaft 202, which rotation is directly communicated to worm gear 204, the telescopic mechanism formed by first telescopic drive shaft 220 and second telescopic tubular drive shaft 221 extends, in the case of rotation in one direction, or contracts, in the case of rotation in the other direction. The external threads of second telescopic tubular drive shaft 221 in turn communicates with drive anchor plate nut 230, which drive anchor plate nut 230 is attached to drive anchor plate 240. Drive anchor plate 240 is, in use, attached to the bone forming a part of the mandible, or other bone to be distracted, by use of anchor screws 241, it being understood that other anchor means may be employed, including surgical pins or nails and screws with hexagonal or other drive bolt heads. The site of the corticotomy or osteotomy lies between base anchor plate 211 and drive anchor plate 240, thereby defining two bone segments. Upon rotation of socket head drive 201 flexible shaft 202 is rotated, which rotation is communicated via worm gear 204 and wheel gear 205 to first telescopic drive shaft 220, which in turn communicates with the internally threaded portion of second telescopic tubular drive shaft 221, and which in turn communicates with drive anchor plate nut 230, such that telescopic drive shafts 220 and 221 extend, causing the distance between base anchor plate 211 and drive anchor plate 240 to increase, thereby distracting or separating the bone segments.

In one alternative configuration of the present invention employing a worm drive, the wheel is internally threaded, and forms a part of a telescoping screw array, and the opposite end of the telescoping screw array is fixed to a drive plate. In a related alternative configuration, a device is constructed employing a worm drive as in FIG. 3, wherein the worm communicates directly with a worm gear, which worm gear in turn communicates with a first wheel gear, which in turn communicates with a second wheel gear. In this configuration, anterior and posterior threaded shafts are provided, one connected to the first wheel gear and the other connected to the second wheel gear, such that there are two telescoping screw drives, one anterior and one posterior. In such case, both can be right-handed threaded, and may be interchangeable. In yet another alternative configuration, the first and second worm gears are internally threaded, and each forms a part of a telescoping screw array. The end of each telescoping screw array is fixed to a drive plate.

Figure 4A:
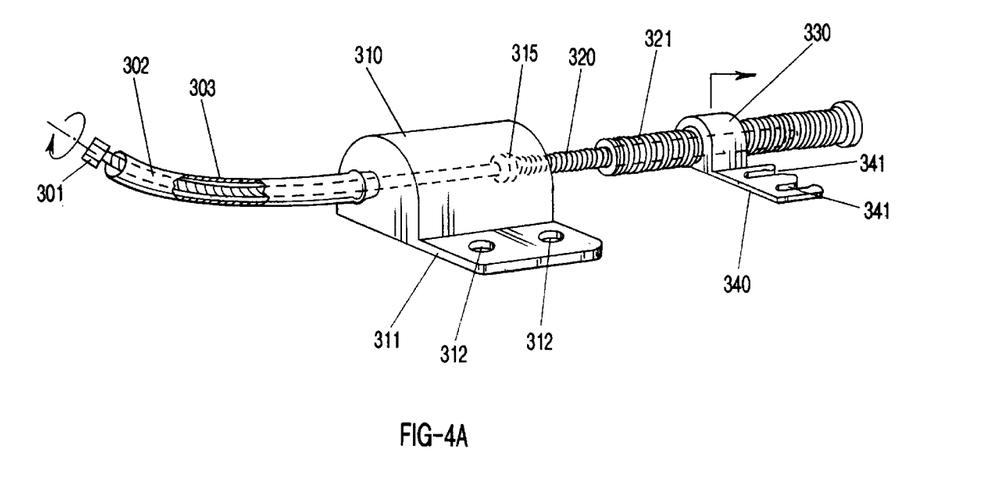
FIGS. 4A and 4B are side views of an alternative embodiment of an apparatus of the present invention for lengthening bones, incorporating a flexible input shaft, linear drive and telescoping screw.

FIG. 4A illustrates an alternative embodiment with a linear drive incorporating a telescoping screw. Flexible shaft 302 is contained within sheath 303, which sheath 303 may be made of any tubing material, including preformed metal tubing or a plastic or composite medical grade tubing. In use of this device for distraction osteogenesis of the mandible, the tubing exits through the cheek within the oral or buccal cavity, and may be accessed therein utilizing a hex driver or other similar driver means, which hex driver engages socket head drive 301 attached to flexible shaft 302. The distal end of flexible shaft 302 is attached to first telescopic drive shaft 320, which in turn communicated with second telescopic tubular drive shaft 321, which second telescopic tubular drive shaft 321 is both internally and externally threaded. First telescopic drive shaft 320 and second telescopic tubular drive shaft 321 are threaded such that upon rotation of flexible shaft 302, which rotation is directly communicated to first telescopic drive shaft 320, the telescoping apparatus formed by shafts 320 and 321 extend. The distal end of flexible shaft 302 is attached to first telescopic drive shaft 320 within housing 310, which housing 310 further comprises a shoulder bearing 315, wherein first telescopic drive shaft 320 includes a shoulder which rests against shoulder bearing 315, such that a thrust load on drive shaft 320 is supported by shoulder bearing 315 in housing 310. Housing 310 is in turn attached to base anchor plate 311, which base anchor plate 311 contains a plurality of holes. In use, base anchor plate 311 is attached to the bone forming a part of the mandible, or other bone to be distracted, through anchor screw holes 312, it being understood that other anchor means may be employed, including slots or other receiving means for screws, surgical pins or nails or screws with hexagonal or other drive bolt heads. The external threads of second telescopic tubular drive shaft 321 communicates with drive anchor plate nut 330, which drive anchor plate nut 330 is attached to drive anchor plate 340. Drive anchor plate 340 is, in use, attached to the bone forming a part of the mandible, or other bone to be distracted, through anchor slots 341 utilizing surgical screws, surgical pins or nails or screws with hexagonal or other drive bolt heads. The site of the corticotomy or osteotomy lies between base anchor plate 311 and drive anchor plate 340, thereby defining two bone segments. Upon rotation of socket head drive 301 flexible shaft 302 is rotated, which rotation is communicated to first telescopic drive shaft 320, which in turn communicates with the internally threaded portion of second telescopic tubular drive shaft 321, and which in turn communicates with drive anchor plate nut 330, such that telescopic drive shaft 321 and drive anchor plate nut 330 extend, causing the distance between base anchor plate 311 and drive anchor plate 340 to increase, thereby distracting or separating the bone segments.

Figure 4B:
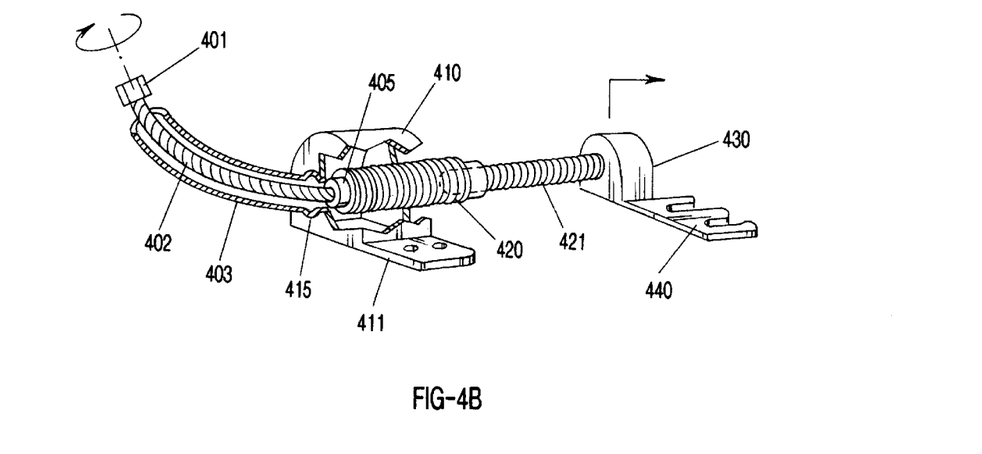

FIG. 4B illustrates an alternative embodiment with a linear drive incorporating a telescoping screw, wherein extension screws or threaded shafts may be employed. Flexible shaft 402 is contained within sheath 403, which sheath 403 may be made of any tubing material, including preformed metal tubing or a plastic or composite medical grade tubing. Sheath 403 is secured by nipple 415. In use of this device for distraction osteogenesis of the mandible, sheath 403 containing flexible shaft 402 exits through the cheek within the oral or buccal cavity, and may be accessed therein utilizing a hex driver or other similar driver means, which hex driver engages socket head drive 401 attached to flexible shaft 402. The distal end of flexible shaft 402 is engagably attached, by means of a hex drive, square drive or other means, to first telescopic tubular drive shaft 420, which is both internally and externally threaded with opposite handed threads, and which in turn communicates with second telescopic drive shaft 421. First telescopic tubular drive shaft 420 and second telescopic drive shaft 421 are threaded such that upon rotation of flexible shaft 402, which rotation is directly communicated to first telescopic tubular drive shaft 420, the telescoping apparatus formed by shafts 420 and 421 extends. First telescopic tubular drive shaft 420 is threadably engaged through its external threads within base anchor plate nut 410, which base anchor plate nut 410 is attached to base anchor plate 411. First telescopic tubular drive shaft 420 further comprises relief shoulder 405, such that at the end of travel threading of shaft 420 through base anchor plate nut 410 is arrested by shoulder 405, and shaft 420 accordingly free-wheels at full extension. In use, base anchor plate 411 is attached to the bone forming a part of the mandible, or other bone to be distracted, by use of anchor screws inserted through the holes, slots or other receiving means provided, it being understood that other anchor means may be employed, including surgical pins or nails and screws with hexagonal or other drive bolt heads. Second telescopic drive shaft 421 is fixed to drive anchor 430, such that shaft 421 may not rotate relative to drive anchor 430. Drive anchor 430 is attached to drive anchor plate 440. Drive anchor plate 440 is, in use, attached to the bone forming a part of the mandible, or other bone to be distracted, by use of anchor screws, it being understood that other anchor means may be employed, including surgical pins or nails and screws with hexagonal or other drive bolt heads. The site of the corticotomy or osteotomy lies between base anchor plate 411 and drive anchor plate 440, thereby defining two bone segments. Upon rotation of socket head drive 401 flexible shaft 402 is rotated, which rotation is communicated to first telescopic tubular drive shaft 420, which in turn communicates with both the second telescopic drive shaft 421 and, through the externally threaded portion of first telescopic tubular drive shaft 420, with base anchor plate nut 410, such that the distance between base anchor plate 411 and drive anchor plate 440 is increased, thereby distracting or separating the bone segments. In use, flexible shaft 402 may be retracted, by disengaging the hex drive, square drive or other means engaging the distal end of flexible shaft 402 to first telescopic tubular drive shaft 420. Thereafter, a length of telescoping extension shaft may be inserted through sheath 403, such that one end of the telescoping extension shaft is engagably attached, by means of the hex drive, square drive or other means provided, to first telescopic tubular drive shaft 420, and the other end of the telescoping extension shaft is engagably attached, by means of the hex drive, square drive or other means provided, to the distal end of flexible shaft 402. By these means, the extension of the telescoping screw assembly may be increased upon continued rotation of socket head drive 401, thereby causing additional distraction.

In each of the embodiments of FIG. 1A through FIG. 4, telescopic drive shafts are provided, it being understood that use of such telescopic drive shafts are one means for providing the maximum extension with the shortest initial length of the device. However, in alternative embodiments of the present invention a simple screw is employed to obtain extension of the device, and any of the embodiments of FIG. 1A through FIG. 4 may be altered such that a screw is provided rather than a telescoping screw assembly.

Figure 5:
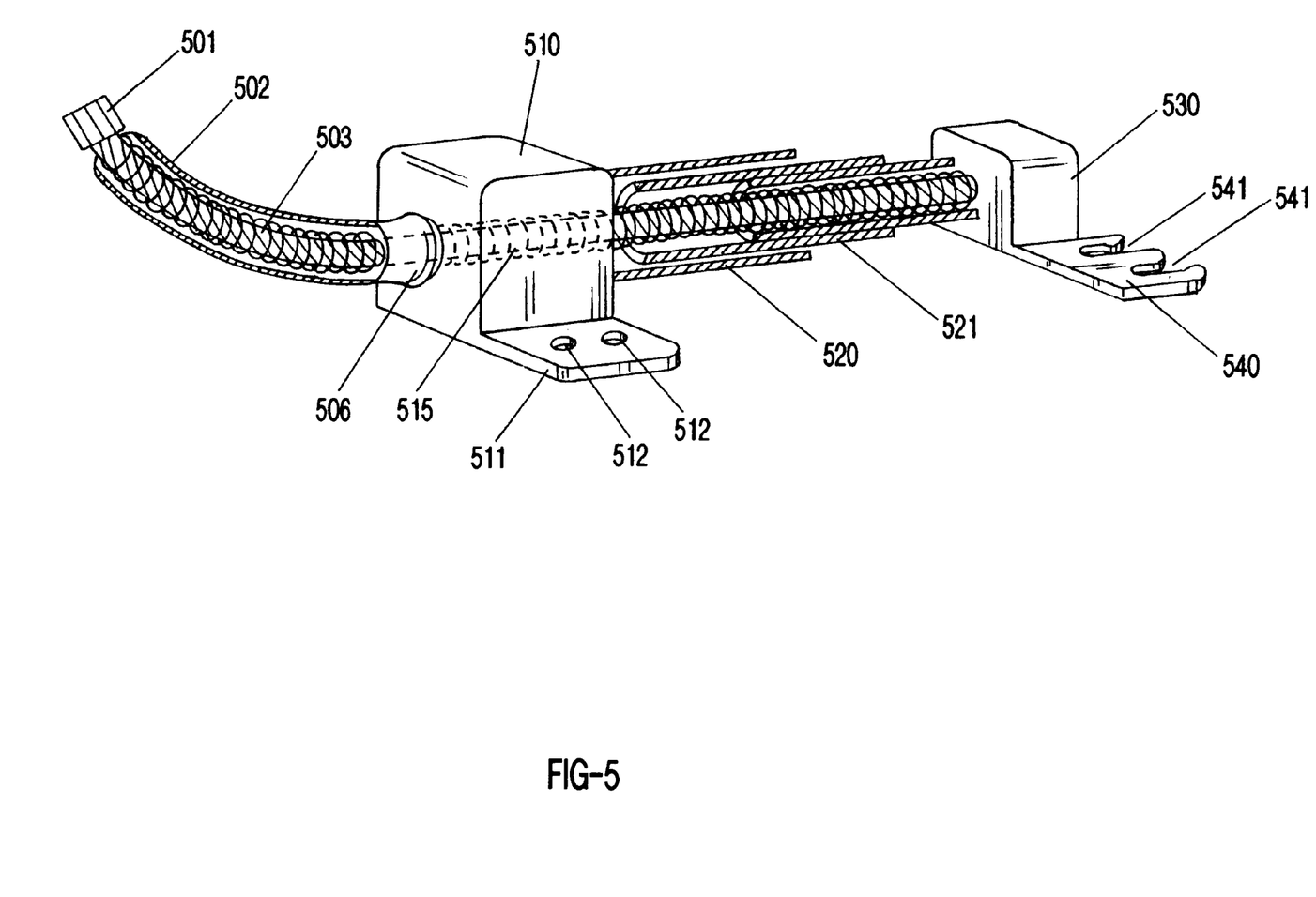
FIG. 5 is a side view of an alternative embodiment of an apparatus of the present invention for lengthening bones, incorporating a flexible input shaft forming the drive screw.

FIG. 5 illustrates an alternative embodiment with a linear drive wherein the flexible shaft comprises a screw. Externally threaded flexible shaft 503 is contained within sheath 502, which sheath 502 may be made of any tubing material, including preformed metal tubing or a plastic or composite medical grade tubing. In use of this device for distraction osteogenesis of the mandible, shaft 503 containing sheath 502 exits through the cheek within the oral or buccal cavity, and may be accessed therein utilizing a hex driver or other similar driver means, which hex driver engages socket head drive 501 attached to externally threaded flexible shaft 503. Externally threaded flexible shaft 503 is threadably engaged within base anchor plate nut 515, which base anchor plate nut 515 is a part of housing 510 and is attached to base anchor plate 511. In use, base anchor plate 511 is attached to the bone forming a part of the mandible, or other bone to be distracted, by use of anchor screws inserted through holes 512, or alternatively through other anchor means, including slots or other receiving means, utilizing surgical screws, surgical pins, nails or screws with hexagonal or other drive bolt heads. In one embodiment of the present invention, the distal end of externally threaded flexible shaft 503 is rotatably attached to drive anchor 530, such that externally threaded flexible shaft 503 may rotate without causing rotation of drive anchor 530. Externally threaded flexible shaft 503 lies within a series of nested telescopic guide tubes 520 and 521, it being understood that there may be more than two such nested telescopic guide tubes, such that externally threaded flexible shaft 503 may freely rotate within such tubes. In one embodiment of the present invention, the outermost nested telescopic guide tube may be affixed to housing 510, and the innermost nested telescopic guide tube may be affixed to drive anchor 510, or vice versa. Drive anchor 530 is attached to drive anchor plate 540. Drive anchor plate 540 is, in use, attached to the bone forming a part of the mandible, or other bone to be distracted, through anchor screws in slots 541, it being understood that other anchor means may be employed, including surgical pins or nails and screws with hexagonal or other drive bolt heads. The site of the corticotomy or osteotomy lies between base anchor plate 511 and drive anchor plate 540, thereby defining two bone segments. Upon rotation of socket head drive 501 externally threaded flexible shaft 503 is rotated, which rotation communicates with base anchor plate nut 510, causing the distance between base anchor plate 511 and drive anchor plate 540 to increase, thereby distracting or separating the bone segments.

The plates used to attach any of the devices of the present invention to bone may be constructed such that one or both plates are initially separate from but attachable to the remainder of the device, and such plate or plates are initially fastened to the bone, by screws or other appropriate means. The remainder of the device, which provides the extension force for distraction, is then attached to the plates. In a preferred embodiment, the device is also detachable from the plate or plates. Any form of coupling or joining means may be employed to couple, fasten, attach or join the plate to the remainder of the device. In use, this permits the surgeon to first attach the plate or plates in the desired location, and to complete the corticotomy or osteotomy, before coupling or joining the remainder of the device to plate or plates. Similarly, removal of the device is also simplified, in that the surgeon may first remove the device by uncoupling or otherwise removing the device from the plate or plates, and then may optionally remove the plate or plates.

In an alternative embodiment of the devices of FIG. 1A through FIG. 5, alternative attachment means of the device to the bone are provided. In one such alternative embodiment, a separate drive anchor plate is attached to the bone forming a part of the mandible, such as the distal attachment site on the descending ramus, or other bone to be distracted, by use of anchor screws inserted through the holes, slots or other receiving means provided, it being understood that other anchor means may be employed, including surgical pins or nails and screws with hexagonal or other drive bolt heads. The remainder of the device is then engaged with the drive anchor plate. By way of example, the device of FIG. 1A may be modified such that the assembly comprising drive anchor plate nut 50 is separate from but engagable to drive anchor plate 51, so that in use a separate drive anchor plate 51 is attached to the bone as heretofore recited, and thereafter the remainder of the device, including drive anchor plate nut 50, is engaged with and attached to separate drive anchor plate 51 through use of engagement pins, clips, bolts or other attachment means known in the art.

In another alternative embodiment, both the base anchor plate and the drive anchor plate may be first attached to the bone forming a part of the mandible, such as the distal attachment site on the ramus, or other bone to be distracted, by use of anchor screws inserted through the holes, slots or other receiving means provided, it being understood that other anchor means may be employed, including surgical pins or nails and screws with hexagonal or other drive bolt heads. The remainder of the device is then engaged with the base anchor plate and the drive anchor plate. By way of example, the device of FIG. 1A may be modified such that the assembly comprising bevel drive unit 25 is separate from but engagable to base anchor plate 40 and the assembly comprising drive anchor plate nut 50 is separate from but engagable to drive anchor plate 51, so that in use both a separate base anchor plate 40 and drive anchor plate 51 are attached to the bone as heretofore recited, and thereafter the remainder of the device is attached to base anchor plate 40 and drive anchor plate 51. In one such embodiment, bevel drive unit 25 is engaged with and attached to base anchor plate 40 and drive anchor plate nut 50 is engaged with and attached to separate drive anchor plate 51, both through use of engagement pins, clips, bolts or other attachment means known in the art. In an alternative embodiment, both base anchor plate 40 and drive anchor plate 51 include engagement pins, which engagement pins may or may not include heads, and bevel drive unit 25 and drive anchor plate nut 50 include receiving slots for the engagement pins, so that in operation the device may be placed between base anchor plate 40 and drive anchor plate 51, and the drive mechanism actuated, such that telescopic drive shafts 30 and 31 extend and the engagement pins are seated within the receiving slots.

In an alternative embodiment of the present invention, the base anchor plate and the drive anchor plate, or either of them, include a lip, such that the lip engages the bone at the site of the bone cut resulting from the corticotomy or osteotomy. By means of the lip, the base anchor plate and the drive anchor plate, or either of them, are fixed relative to the site of the corticotomy or osteotomy, thereby preventing migration of the device through the bone upon extension of the device.

In an alternative embodiment of the present invention, of particular utility when a detachable plate or plates are employed, the plate or plates are constructed of a bioresorbable material. In general, the devices of the present invention are made of either biocompatible metals and metal alloys, such as commercially pure titanium, stainless steel or cobalt chrome molybdenum, or are made out of a biocompatible plastic or other suitable synthetic material, such as Delrin®. However, at least a portion of the device, and preferably the plate or plates, may be constructed of a bioresorbable material, such as the non-reinforced lactide and glycolide copolymer composition taught in U.S. Pat. No. 5,569,250, the teachings of which are incorporated herein by reference. With the use of such bioresorbable plates, there is no need to remove the plates following distraction and consolidation of the bone, and the remainder of the device is surgical removed, with the plates left in place. Optionally, the bioresorbable plates are combined with bioresorbable surgical fasteners, such as bioresorbable bone screws, or are combined in a composite device, with metallic or metallic allow surgical fasteners, such as bone screws, of the materials previously discussed, or any other appropriate materials known in the art.

In an alternative configuration, any of the devices of FIGS. 1 through 4 can be configured so as to employ a compression spring within the drive mechanism. Without elasticity, the distractor translates turns of the input drive shaft directly into increased bone gap. Thus, the bone lengthening process occurs in a pulsing pattern, with an incremental jump (e.g., 1 mm) occurring daily at the time the input drive is activated. By inserting a spring of appropriate stiffness, the displacement introduced by the twist of the drive shaft is primarily converted to an initial displacement or compression of the spring. The spring then exerts a steady spreading force upon the two bone segments, causing them to spread slowly apart in a continuous manner over the interval of time between adjustments.

In an alternative configuration of a screw-actuated linear distraction device of the present invention, the flexible shaft is fixed to a first spur gear contained within a housing, such that upon rotation of the flexible shaft the first spur gear rotates, and drives a second spur gear, which second spur gear is internally threaded, such that upon rotation of the second spur gear a threaded shaft extends, in the direction of distraction desired, the threaded shaft being fixed to a drive plate, which drive plate may include an angled slot for receiving a surgical screw or pin, or a keyhole for receiving a surgical screw or pin, or other bone fixation means, and optionally a locking detente or other locking means for locking the surgical screw or pin in place. The housing is itself attached, either directly or through use of a surgical plate or other suitable means, to the bone forming a part of mandible, by surgical screws, surgical pins, surgical adhesives or other means known in the art.

Generally, with any of the devices of the present invention distraction is at a rate of approximately 1 mm per day, but this rate may be varied as appropriate given the age, condition of the patient and other variables. The length of distraction is dependent, in part, on the maximum extension of the distraction device, but distraction of up to 20 to 40 mm or greater is possible. Distraction is continued until the desired amount of bone growth is obtained. The devices of the present invention are left in place during a period of stabilization of the bone, which can take from one to four months. During the period of stabilization the flexible shaft and flexible sheath, if provided, is optionally removed, to improve patient comfort in that the shaft and sheath no longer terminate within the oral cavity. After the bone has stabilized the devices of the present invention are surgically removed.

An alternative device for bidirectional distraction permits simultaneous but individually adjustable horizontal and vertical distraction. Such devices incorporate two flexible input shafts, such as shaft 202 of FIG. 3, two right angle worm drives, such as the worm drive depicted in FIG. 3, and two telescoping screw drives, such as the telescoping screw drive depicted in FIG. 3. In use, each flexible shaft is individually rotated by engaging the socket head drive with a wrench, driver or similar device. The flexible shafts each terminate in a separate gear housing, it being understood that each gear housing may be any shape desired, wherein is contained an angled gear drive, which may be a reducing worm gear drive, or a bevel, helical or hypoid drive. The gear housings are themselves not attached to the bone, or otherwise anchored. If a worm drive is employed, the distal end of each flexible shaft is attached to a worm which communicates to a pinion gear, each of which pinion gears in turn communicate with two threaded shafts. An anterior threaded shaft terminates in a first fixation plate located on the anterior bone segment, and a posterior threaded shaft terminates in a second fixation plate located on a posterior bone segment. In the event that the device is employed in a surgical procedure wherein two bones cut are performed, such that there is a resulting floating or isolated bone segment, a means for fixation to the floating or isolated bone segment is also provided, which means for fixation is most preferably located at or between the anterior and posterior gear housings. The means for fixation to the bone segment may be by one or more surgical screws, pins or other means known in the art. After surgical placement, and during the distraction process, the relative amounts of horizontal and vertical distraction may each be independently controlled, by specifying the number of rotations to be applied to each of the flexible drive shafts. The device, and other devices of the present invention, may terminate at each end with an angled slot for receiving a surgical screw and a locking detente for locking the surgical screw in place, or may terminate with a surgical plate on the proximal end, and a keyhole and locking detente at the distal end, or any combination or permutation thereof.

In an alternative configuration of a device for bidirectional distraction, incorporating a right angle drive, a fixed guide rail is provided for distraction along a predetermined path, and optionally a compression spring for gradual application of distraction force. This device includes a flexible shaft, terminating in a socket head drive which in turn is attached to a flexible shaft, and which may be optionally enclosed within a flexible sheath. In use, the flexible shaft is rotated by engaging the socket head drive with a wrench, driver or similar device. The flexible shaft terminates in a rectangular gear housing, it being understood that the gear housing may be any shape desired, wherein is contained an angled gear drive, which may be a reducing gear drive, and may be a worm, helical, bevel or hypoid gear drive, or any drive means known in the art. In yet other alternative configurations, the device incorporates a straight drive or a geared linear drive. The housing is itself attached to the bone forming a part of mandible, by surgical screws, surgical pins, surgical adhesives or other means known in the art, which attachment may be direct or through a surgical plate or other means. The distal end of the flexible shaft is attached to the drive assembly, which in turn communicates with a threaded shaft. The threaded shaft in turn is threaded through a threaded hole in a drive plate, which drive plate contains an additional unthreaded hole through which passes the guide rail, which guide rail also passes through a channel, slot or hole provided therefore in the gear housing. The guide rail may be formed such that it cannot rotate within the unthreaded hole in the drive plate or the channel, slot or hole in the gear housing, but may only slide through such hole, channel, or slot. In an alternative configuration, more than one guide rail may be employed, such as two parallel guide rails. The guide rail or rails are movably attached to the fixation plate, which fixation plate includes an angled slot for receiving a surgical screw and a locking detente for locking the surgical screw in place. The fixation plate communicates by means of a compression spring with the drive plate, such that on rotation of the flexible shaft, the torque is communicated to the threaded shaft, and thence communicated to the drive plate, so that on rotation the drive plate separates from the gear housing, and the compression spring communicates compressive or displacement force to the fixation plate, causing the fixation plate and gear housing to separate along a path determined by the guide rail. The device is placed, during surgery, so that the corticotomy is located between the gear housing and the fixation plate, such that on rotation of the flexible shaft the telescoping screw array extends and distracts, or separates, the space between the two cut ends of the bone. The device may terminate with a surgical plate on the proximal end, and an angled slot for receiving a surgical screw with a locking detente for locking the surgical screw in place at the distal end, with a keyhole and detente assembly, or any other means known or any combination or permutation thereof.

The invention further provides a programmable, coordinated multi-axis drive, optionally with remote monitoring. Drive motors are employed, which utilize any drive engine motor known to the art, including an electrical motor, with internal electric power supply or externally supplied power through radio frequency or magnetic field means, or employ drive engine motors powered by chemical means, compressed fluids means, compressed gas means, preloaded spring means, shape memory alloy means or other motive means known in the art. If stored energy means are used, such as compressed fluid means, compressed gas means, preloaded spring means and the like, then the drive engine may meter the amount of energy released, through electrical or other means. Each of the drive motors may be independently controllable, to provide coordinated distraction along multiple axes. In one embodiment force transducers are employed, and preferably a force transducer associated with each drive motor, which measures the force required to obtain distraction. Utilizing the force transducers, with appropriate communications or control means it is possible to adjust the motive power applied to the motors, either on external command or through programmed instructions. Displacement transducers may also be employed, which measures the relative position of the proximal mandible section to the distal ramus section, so that the amount of distraction obtained can be independently measured. The information on distraction forces and displacement or lengthening can be transmitted, by any means known to the art, including radio frequency means and ultrasonic means, to a receiver, to allow monitoring of the rate, distance and direction of distraction, and allow variation in the control of each of the motors to obtain optimal distraction.

The invention further provides an alternative device for unidirectional or bidirectional distraction, incorporating a hydraulic drive mechanism and optionally a fixed guide rail for distraction along a predetermined path. A flexible fluid reservoir is provided, which reservoir may incorporate a squeeze-bulb pump with a one-way value, such that upon compression of the squeeze-bulb pump, such as by pressing with a finger or thumb, a portion of the fluid provided therein enters the flexible hydraulic bellows. The flexible hydraulic bellows may optionally be movably connected to a guide rail by a plurality of connector means, such as rings attached to the bellows through which passes the guide rail, such that upon extension of the flexible hydraulic bellows its motion is constrained to follow the path of the guide rail. The flexible hydraulic bellows terminates in a housing, which may optionally contain the flexible fluid reservoir or squeeze-bulb pump, it being understood that the housing may be any shape desired suitable to the purpose described. The housing is itself attached to the bone forming a part of mandible, by surgical screws, surgical pins, surgical adhesives or other means known in the art, which attachment may be direct or through a surgical plate or other means. The flexible fluid reservoir and squeeze-bulb pump may be connected to the flexible hydraulic bellows by means of a tube and may include one or more one-way valves, permitting fluid to enter the bellows but not return to the flexible fluid reservoir or squeeze-bulb pump. The flexible fluid reservoir and squeeze-bulb pump may be located in any subcutaneous location desired, connected by a tube as provided, or may be located outside the body, connected via the tube as provided which transits the skin. The distal end of the flexible hydraulic bellows is connected to a drive plate, which drive plate contains an unthreaded hole through which passes the guide rail, which guide rail also passes through a channel, slot or cylindrical hole provided therefore in the housing. The drive plate may include one or more angled slots for receiving surgical screws or pins and a locking detente for locking the surgical screws or pins in place, or other means for connecting the drive plate to the bone, or in the alternative, the drive plate may be connected by a spring or similar compressive means, which in turn communicates with a bone anchor plate, which includes one or more angled slots for receiving surgical screws or pins and a locking detente for locking the surgical screws or pins in place, or other means for connecting the drive plate to the bone. Upon introduction of fluid to the flexible hydraulic bellows, the hydraulic bellows is extended, thereby causing the drive plate to separate from the housing along a path determined by the guide rail. The device is placed, during surgery, so that the corticotomy is located between the housing and the drive plate, or if a bone anchor plate is provided, between the housing and the bone anchor plate, such that on extension of the bellows the device distracts the space between the two cut ends of the bone. The device may terminate with a surgical plate on the proximal housing end, and with an angled slot for receiving a surgical screw with a locking detente for locking the surgical screw in place at the distal end, with a keyhole and detente assembly, or by any other means known or any combination or permutation thereof.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references cited above are hereby incorporated by reference.

I claim:

1. A device for lengthening bone by distraction osteogenesis comprising:
    a telescoping screw assembly comprising at least two members, a first member threaded shaft cooperatively engaged with the inner screw thread of a second member tubular screw having an outer screw thread and an inner screw thread;
    a nut for engaging the outer screw thread of the second member tubular screw connected to and fixed in position relative to a first securing means for securing to the bone; and
    an angled drive means for providing a drive force to the telescoping screw assembly and in communication with the first member threaded shaft and fixed in position relative to second securing means for securing to the bone.

2. The device of claim 1, wherein the telescoping screw assembly comprises one or more additional members consisting of a tubular screw having an outer screw thread and an inner screw thread and threadably engaged and disposed between said first member threaded shaft and said second member tubular screw.

3. The device of claim 1, wherein the first securing means further comprises a plate comprising means for fastening to bone.

4. The device of claim 3, wherein the first securing means further comprises engagement means for removably attaching the said nut to the plate, the plate comprising an engagable assembly, wherein the said plate comprising an engagable assembly is secured to the bone prior to attaching the said nut to the said plate, and wherein the said nut may be subsequently unattached from the said plate.

5. The device of claim 4, wherein the plate is a bioresorbable plate.

6. The device of claim 4, wherein the plate is attached to the bone by use of bioresorbable surgical fasteners.

7. The device of claim 1, wherein the angled drive means comprises an angled gear drive.

8. The device of claim 7, wherein the angled gear drive is a reducing gear drive.

9. The device of claim 7, wherein the angled gear drive is a worm, helical, bevel or hypoid gear drive.

10. The device of claim 1, wherein the angled drive means is at least partially enclosed within a housing, the housing further comprising the second securing means for securing to the bone.

11. The device of claim 1, further comprising a tongue, slidably engaged to the first securing means and the second securing means through a slot provided therefore in the first securing means and second securing means, whereby rotation of the first securing means relative to the second securing means is prevented.

12. A device for lengthening bone by distraction osteogenesis comprising:
    a first telescoping screw assembly comprising at least two members, a first member threaded shaft cooperatively engaged with the inner screw thread of a second member tubular screw having an outer screw thread and an inner screw thread;
    a second telescoping screw assembly comprising at least two members, a first member threaded shaft cooperatively engaged with the inner screw thread of a second member tubular screw having an outer screw thread and an inner screw thread;
    a first nut assembly for engaging the outer screw thread of the second member tubular screw of the first telescoping screw assembly connected to and fixed in position relative to a first securing means for securing to the bone;
    a second nut assembly for engaging the outer screw thread of the second member tubular screw of the second telescoping screw assembly connected to and fixed in position relative to a second securing means for securing to the bone; and
    an angled drive means for providing a drive force to the first and second telescoping screw assemblies and in communication with the first member threaded shaft of each of the first and second telescoping screw assemblies.

13. The device of claim 12, wherein either the first or the second telescoping screw assembly comprises one or more additional members consisting of a tubular screw having an outer screw thread and an inner screw thread and threadably engaged and disposed between said first member threaded shaft and said second member tubular screw.

14. The device of claim 12, wherein the first securing means and second securing means further comprises a plate comprising means for fastening to bone.

15. The device of claim 12, wherein the angled drive means is an angled gear drive.

16. The device of claim 15, wherein the angled gear drive is a worm, helical, bevel or hypoid gear drive.

17. The device of claim 12, wherein the angled drive means is at least partially enclosed within a housing, the housing further comprising third securing means for securing the housing to the bone.

18. A device for lengthening bone by distraction osteogenesis comprising:
    a telescoping screw assembly comprising at least two members, a first member threaded shaft cooperatively engaged with the inner screw thread of a second member tubular screw having an outer screw thread and an inner screw thread;
    a nut for engaging the outer screw thread of the second member tubular screw connected to and fixed in position relative to a first securing means for securing to the bone; and
    a linear drive means for providing a drive force to the telescoping screw assembly and in communication with the first member threaded shaft and fixed in position relative to second securing means for securing to the bone.

19. The device of claim 18, wherein the telescoping screw assembly comprises one or more additional members consisting of a tubular screw having an outer screw thread and an inner screw thread and threadably engaged and disposed between said first member threaded shaft and said second member tubular screw.

20. The device of claim 18, wherein the first securing means further comprises a plate comprising means for fastening to bone.

21. The device of claim 20, wherein the first securing means further comprises engagement means for removably attaching the said nut to the plate, the plate comprising an engagable assembly, wherein the said plate comprising an engagable assembly secured to the bone prior to attaching the said nut to the said plate, and wherein the said nut may be subsequently unattached from the said plate.

22. The device of claim 20 wherein the plate is a bioresorbable plate.

23. The device of claim 20, wherein the plate is attached to the bone by use of bioresorbable surgical fasteners.

24. The device of claim 18, wherein the linear drive means further comprises a flexible shaft in communication with the first member threaded shaft and partially enclosed within a housing, the housing further comprising a plate comprising the second securing means for securing to the bone.

25. The device of claim 18, further comprising a tongue, slidably engaged to the first securing means and the second securing means through a slot provided therefore in the first securing means and second securing means, whereby rotation of the first securing means relative to the second securing means is prevented.

26. A device for lengthening bone by distraction osteogenesis comprising:

a telescoping screw assembly comprising at least two members, a first member tubular screw having a first end and a second end and an outer screw thread and an inner screw thread, which inner screw thread is cooperatively engaged with threads of a second member threaded shaft;

a nut for engaging the outer screw thread of the first member tubular screw connected to and fixed in position relative to a first securing means for securing to the bone;

a drive means for providing a drive force to the telescoping screw assembly and in communication with the first end of the first member tubular screw; and a second securing means for securing to the bone, the second member threaded shaft being fixed to said second securing means.

27. The device of claim 26, wherein the telescoping screw assembly comprises one or more additional members consisting of a third member threaded shaft with a first end and second end cooperatively engagable with the inner screw thread of the first member tubular screw, wherein the drive means is detachable from the first end of the first member tubular screw, the second end of the third member threaded shaft is attachable to the said first end of the said first member tubular screw, and the said drive means is attachable to the first end of the said third member threaded shaft.

28. The device of claim 26, wherein the first securing means further comprises a plate comprising means for fastening to bone.

29. The device of claim 28, wherein the first securing means further comprises engagement means for removably attaching the said nut to the plate, the plate comprising an engagable assembly, wherein the said plate comprising an engagable assembly is secured to the bone prior to attaching the said nut to the said plate, and wherein the said nut may be subsequently unattached from the said plate.

30. The device of claim 28, wherein the plate is a bioresorbable plate.

31. The device of claim 28, wherein the plate is attached to the bone by use of bioresorbable surgical fasteners.

32. The device of claim 26, wherein the drive means further comprises a flexible shaft in communication with the first end of the first member tubular screw.

33. The device of claim 26, further comprising a tongue, slidably engaged to the first securing means and the second securing means through a slot provided therefore in the first securing means and second securing means, whereby rotation of the first securing means relative to the second securing means is prevented.

34. The device of claim 1, further comprising a drive sheath providing access to the angle drive means and attached to the angled drive means, whereby a drive force can be provided to the angled drive means through the drive sheath.

35. The device of claim 1, wherein the angle of the angled drive means is adjustable.

36. The device of claim 1, wherein the angled drive means further comprises a flexible shaft in communication with the first member threaded shaft and partially enclosed within a housing, the housing further comprising a plate comprising the second securing means for securing to the bone.

* * * * *